United States Patent [19]
Hance et al.

[11] Patent Number: 5,906,718
[45] Date of Patent: *May 25, 1999

[54] ELECTROCHEMICAL GAS SENSOR FOR THE DETECTION OF NITROGEN DIOXIDE

[75] Inventors: Glen W. Hance, Grove City; Joseph D. Jolson, Pittsburgh; Towner B. Scheffler, Butler, all of Pa.

[73] Assignee: Mine Safety Appliances Company, Pittsburgh, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/910,421

[22] Filed: Aug. 13, 1997

Related U.S. Application Data

[63] Continuation of application No. 08/426,271, Apr. 21, 1995, abandoned.

[51] Int. Cl.[6] .................................................. G01N 27/404
[52] U.S. Cl. ......................... 204/412; 204/294; 204/415; 204/431; 204/432; 205/781
[58] Field of Search .................... 204/412, 415, 204/431, 432; 205/781

[56] References Cited

U.S. PATENT DOCUMENTS

| | | | |
|---|---|---|---|
| Re. 31,915 | 6/1985 | Oswin et al. | 204/432 |
| 2,861,926 | 11/1958 | Jacobson | 204/432 |
| 3,787,308 | 1/1974 | Malaspina et al. | 204/432 |
| 3,824,166 | 7/1974 | Deibert | 204/432 |
| 3,974,040 | 8/1976 | Siebke et al. | 204/432 |
| 4,132,616 | 1/1979 | Tantrum et al. | 204/195 |
| 4,324,632 | 4/1982 | Tantrum et al. | 204/195 |
| 4,406,770 | 9/1983 | Chan et al. | 204/415 |
| 4,474,648 | 10/1984 | Tantrum et al. | 204/1 |
| 4,525,266 | 6/1985 | Schmidt et al. | 204/415 |
| 4,571,292 | 2/1986 | Liu et al. | 204/415 |
| 4,639,306 | 1/1987 | Tomasovic et al. | 204/432 |
| 4,790,925 | 12/1988 | Miller et al. | 204/415 |
| 5,071,526 | 12/1991 | Pletcher et al. | 205/781 |
| 5,284,566 | 2/1994 | Cuomo et al. | 204/432 |
| 5,338,429 | 8/1994 | Jolson et al. | 204/432 |
| 5,512,159 | 4/1996 | Yoshioka et al. | 204/403 |
| 5,538,620 | 7/1996 | Nikolskaja | 205/782 |

FOREIGN PATENT DOCUMENTS

| | | |
|---|---|---|
| 0496527 | 7/1992 | European Pat. Off. . |
| 93/10444 | 5/1993 | WIPO . |

OTHER PUBLICATIONS

Cao, Z and Stetter, J.R., "Amperometric Gas Sensors", pp. 43–57 date unavailable.

*Primary Examiner*—T. Tung
*Attorney, Agent, or Firm*—James G. Uber; Henry E. Bartony, Jr.

[57] ABSTRACT

The present invention provides an electrochemical gas sensor for the detection of nitrogen dioxide comprising a housing and a working electrode and a counter electrode disposed within the housing. Each of the working electrode and the counter electrode are fabricated from an electrically conductive carbon. The present sensor also preferably comprises a reference electrode fabricated from an electrically conductive carbon.

19 Claims, 2 Drawing Sheets

ELECTROCHEMICAL GAS SENSOR FOR THE DETECTION OF NITROGEN DIOXIDE

This application is a continuation of application Ser. No. 08/426,271 filed on Apr. 21, 1995, now abandoned.

FIELD OF THE INVENTION

The present invention relates to an electrochemical gas sensor, and more particularly to an electrochemical gas sensor for the detection of nitrogen dioxide ($NO_2$).

BACKGROUND OF THE INVENTION

In an electrochemical gas sensor, the gas to be measured typically diffuses from the atmosphere into the sensor housing through a gas porous or gas permeable membrane to a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working and counter electrodes.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte gas over the concentration range of interest.

In addition to a working electrode and a counter electrode, an electrochemical sensor often includes a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

Electrical connection between the working electrode and the counter electrode is maintained through an electrolyte. The primary functions of the electrolyte are: (1) to efficiently carry the ionic current; (2) to solubilize the analyte gas; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

Electrochemical gas sensors of the type discussed above are generally disclosed and described in U.S. Pat. Nos. 4,132,616, 4,324,632, 4,474,648; and in European Patent Application No. 0 496 527 A1. A comprehensive discussion of electrochemical gas sensors is also provided in a paper by Cao, Z. and Stetter, J. R., entitled "Amperometric Gas Sensors," the disclosure of which is incorporated herein by reference.

In general, the electrodes of an electrochemical cell provide a surface at which an oxidation or a reduction reaction occurs to provide a mechanism whereby the ionic conduction of the electrolyte solution is coupled with the electron conduction of the electrode to provide a complete circuit for a current. It is generally believed that the half cell reactions of the working electrode and the counter electrode, respectively, for nitrogen dioxide ($NO_2$) electrochemical gas sensors (using $H_2SO_4$ as the electrolyte) are as follows:

$$NO_2 + 2H^+ + 2e^- \rightleftharpoons NO + H_2O$$

$$H_2O \rightleftharpoons \tfrac{1}{2}O_2 + 2H^+ + 2e^-$$

The above reactions result in the following net cell reaction:

$$NO_2 \rightleftharpoons NO + \tfrac{1}{2}O_2$$

The measurable current arising from the above cell reaction is directly proportional to the rate of reaction. Preferably, therefore, a high reaction rate is maintained in the electrochemical cell. For this reason, the counter electrode and/or the working electrode of the electrochemical cell generally comprise an appropriate electrocatalyst on the surface thereof to enhance the reaction rate. If the reaction rate of either half cell reaction is impeded, resulting in a low exchange current density, the equilibrium current of the electrochemical cell may be easily perturbed during measurement. Such deviation can result in undesirable side reactions and/or nonlinear behavior over the range of nitrogen dioxide concentrations desired to be detected.

The phrase "exchange current density" as used in connection with the present invention refers generally to the normalized exchange current or exchange current per unit area. The exchange current is generally defined as the level of balanced faradaic activity or net chemical change occurring at an electrode when the net current is zero. The exchange current is proportional to the native rate at which either, or in the ideal case, both, the anodic and cathodic reactions occur for a given chemical species at an electrode. The lower the exchange current density, the more sluggish is the electrode reaction, and the more difficult it is to obtain useful output from the system. On the other hand, the larger the exchange current, the faster the electrode reaction occurs. At high exchange currents, large currents can be supplied by the system with ease. "The exchange current can be viewed as a kind of 'idle speed' for charge exchange across the electrode-electrolyte interface." Bard, A. J. and Faulkner, L. R., Electrochemical Methods, Fundamentals and Applications, John Wiley & Sons, New York, pp. 100–107 (1980).

To achieve adequate exchange current density in existing electrochemical sensors for detecting nitrogen dioxide, the counter electrode generally comprises an electrocatalyst such as, for example, platinum (Pt) or iridium (Ir), suitable to catalyze the oxidation reaction occurring at that electrode. Such an electrochemical sensor is presently available, for example, from City Technology of Portsmouth, England. In the City Technology sensor (that is, the Nitrogen Dioxide CiTicel), the working and reference electrodes are fabricated from carbon, while the counter electrode comprises a Pt electrocatalyst.

As somewhat evident from the above discussion, the type, rate, and efficiency of the chemical reactions within an electrochemical gas sensor are controlled, in significant part, by the material(s) used to make the working electrode and counter electrode. Indeed, extensive research efforts are expended to develop improved working electrodes, counter electrodes and electrochemical systems generally. See Cao, supra, at 49. As part of these efforts, manufacturers of electrochemical sensors continuously attempt to simplify the manufacturing process and to reduce the costs involved therein, while maintaining suitable sensor performance specifications.

It is desirable, therefore, to develop new electrodes and electrode combinations for use in electrochemical gas sensors for the detection of nitrogen dioxide which achieve the above-referenced goals.

SUMMARY OF THE INVENTION

Accordingly, the present invention provides an electrochemical gas sensor for the detection of nitrogen dioxide that may be manufactured in fewer steps and at less cost than electrochemical gas sensors presently available. In general, the electrochemical gas sensor of the present invention comprise a housing, a working electrode and a counter electrode, wherein the counter electrode is fabricated from an electrically conductive carbon. Preferably, the working electrode is also fabricated from an electrically conductive carbon.

Applicants have discovered that the use of a metallic electrocatalyst is unnecessary when the counter electrode for a nitrogen dioxide electrochemical sensor is fabricated from an electrically conductive carbon. Preferably, therefore, the electrochemically active surface of the counter electrode of the present invention consists essentially of an electrically conductive carbon. Similarly, the electrochemically active surface of the working electrode also preferably consists essentially of an electrically conductive carbon. Preferably, the electrochemically active surface of the working electrode consists essentially of the same electrically conductive carbon as the electrochemically active surface of the counter electrode.

Electrochemical sensors of the present invention preferably further comprise a reference electrode which is also fabricated from an electrically conductive carbon. The counter electrode of the present invention is preferably shaped in the general form of an annulus, while the reference electrode is preferably shaped in a generally circular, disk-shaped form. Because the present counter electrode and the present reference electrode may be fabricated from the same electrically conductive carbon, the counter electrode and the reference electrode may be manufactured in a single process. For example, the reference electrode may comprise a disk of electrically conductive carbon removed from a larger diameter disk of electrically conductive carbon in forming the annular counter electrode.

As used in connection with the present invention, the phrase "electrically conductive carbon" refers generally to carbons with resistances in the range of approximately 0.2 kΩ to 180 kΩ. The carbons used in fabrication of electrodes for use in the present invention preferably also have specific surfaces in the range of 4.6 m$^2$/g to 1500 m$^2$/g. In fabricating the working electrode, the counter electrode and the reference electrode of the present invention, the electrically conductive carbon is preferably fixed upon a water resistant membrane such a GoreTex® film.

Unlike the present invention, the different fabrication materials of the counter electrode and the reference electrode of existing electrochemical sensors for detecting nitrogen dioxide require that those electrodes be manufactured in separate processes. By elimination of the requirement for separate processing of the counter electrode and the reference electrode, the present invention significantly reduces manufacturing costs. Moreover, the surprising discovery in the present invention that costly electrocatalysts such as platinum may be eliminated from counter electrodes (as well as working electrodes) used in the detection of nitrogen dioxide provides further cost savings.

Further, the use of an electrically conductive carbon counter electrode in the present invention reduces the likelihood of undesirable side reactions common to the use of strongly electrocatalytic materials such as platinum. Interferent studies performed with sensors of the present invention show the sensors of the present invention to be less susceptible to erroneous results arising from the presence of interferent gases than existing sensors. Still further, the sensors of the present invention provide a substantially linear signal over a broader range of nitrogen dioxide concentration that existing sensors.

DETAILED DESCRIPTION OF THE INVENTION

Figure 1:
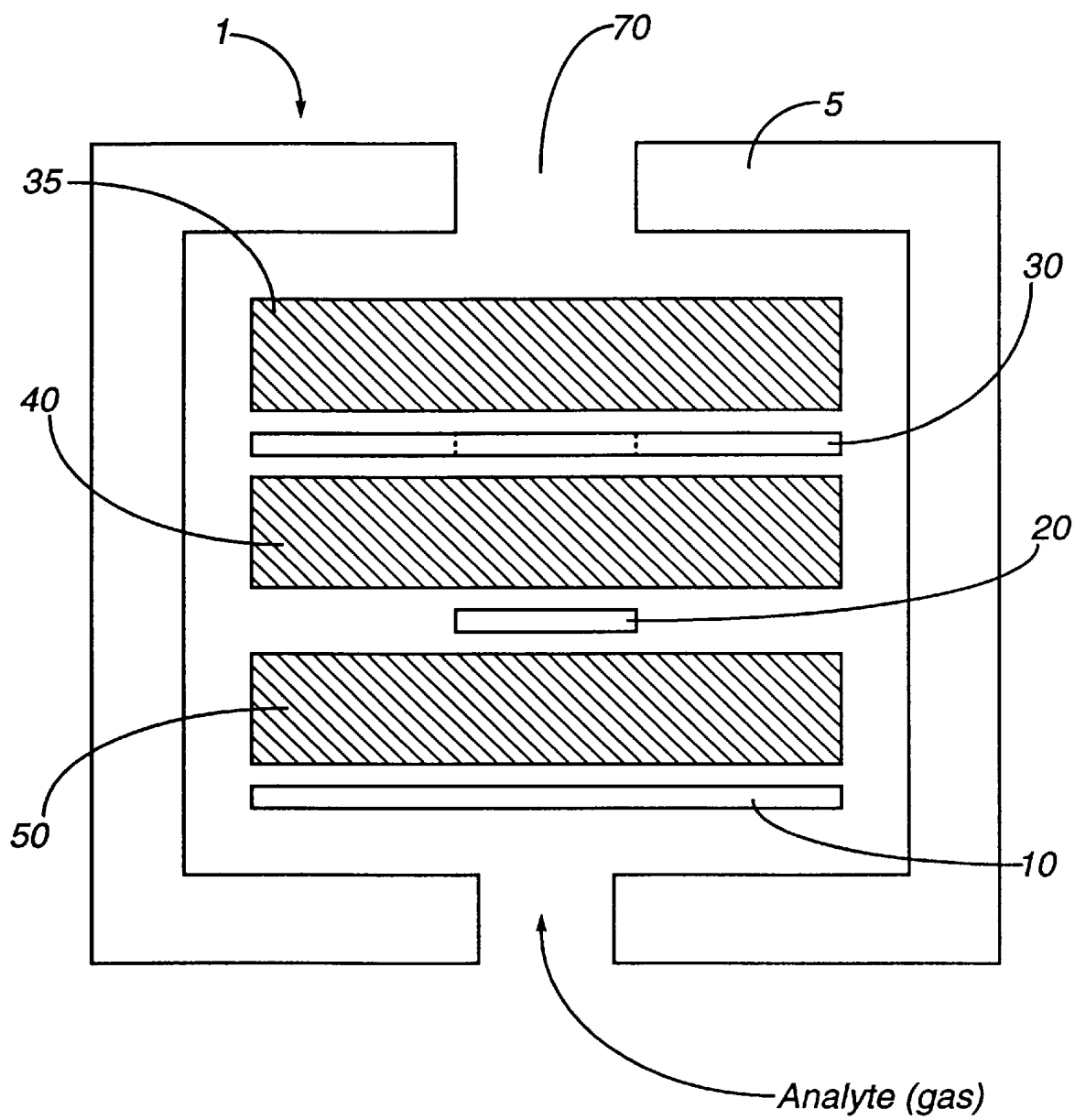
FIG. 1 illustrates schematically a cross-sectional view of an electrochemical gas sensor of the present invention.

As seen in FIG. 1, electrochemical nitrogen dioxide sensor 1 preferably comprises a housing 5, enclosing a working electrode 10, a reference electrode 20 and a counter electrode 30. In fabricating electrochemical nitrogen dioxide sensors 1 for use in the present studies a porous spacer or wick 35 was first placed within housing 5. Counter electrode 30 was then placed into housing 5. A porous spacer or wick 40 was preferably then placed within housing 5 followed by reference electrode 20. A porous wick 50 was subsequently placed within housing 5 followed by working electrode 10.

After placement of working electrode 10 within housing 5, the perimeter of working electrode 10 was heat sealed to housing 5. The interior of housing 5 was then filled with an electrolyte such as H$_2$SO$_4$ via opening 70. Upon filling of the interior of housing 5 with electrolyte, opening 70 was sealed, preferably via heat sealing using a water resistant membrane such as a GoreTex film (not shown). In the present studies, housing 5 was also placed within an outer housing (not shown). The electrical leads of working electrode 10 and reference electrode 20 were shorted with a "shorting-clip". A detailed discussion of a preferred assembly for electrochemical gas sensor 1 is set forth in U.S. Pat. No. 5,338,429, the disclosure of which is incorporated herein by reference.

Wicks 40 and 50 operate to prevent physical contact of the electrodes but allow the liquid electrolyte to contact the electrodes and thereby provide ionic connection between working electrode 10 and counter electrode 30. Preferably, the electrolyte used in electrochemical nitrogen dioxide sensor 1 is H$_2$SO$_4$.

Electrodes for use in electrochemical sensors 1 for the present studies were preferably fabricated under the following methodology. Working electrode 10, reference electrode 20 and counter electrode 30 were preferably fabricated via silk screen deposition of a carbon ink upon a GoreTex film as known in the art. As known in the art, GoreTex films provide a very good support for an electrochemically active material and also provide a good diffusion barrier, allowing analyte gas to diffuse into the electrochemical sensor while preventing escape of electrolyte. The carbon may also be deposited using hand painting techniques as known in the art. Preferably, a film having a thickness in the range of approximately 1 to 10 mil is deposited. More preferably, a film having a thickness in the range of approximately 3 to 6 mil is deposited.

After deposition of the conductive carbon, the film was sintered to fix the carbon thereon such as is described in U.S. Pat. No. 4,790,925, the disclosure of which is incorporated herein by reference. After sintering, working electrode 10 and counter electrode 30 were stamped/cut out of the film, preferably in a circular shape.

Figure 2:
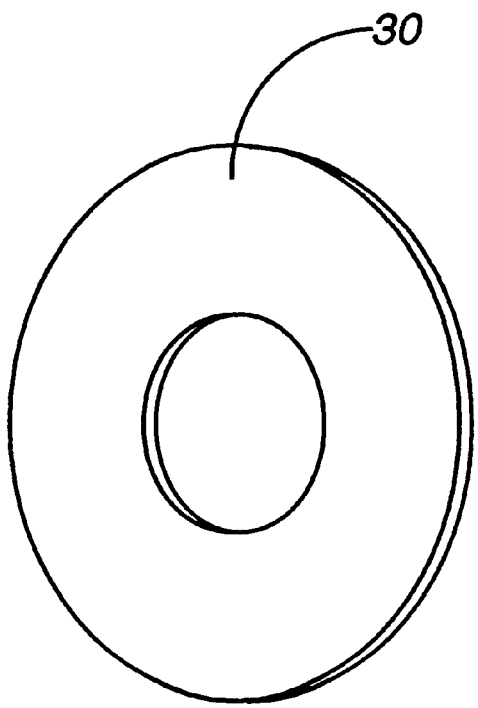
FIG. 2 illustrates a perspective view of an embodiment of the present counter electrode.
Figure 3:
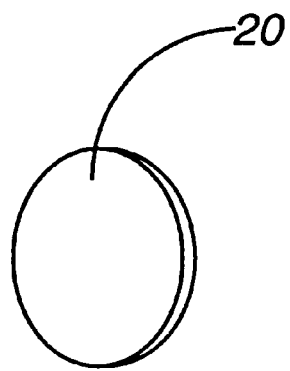
FIG. 3 illustrates a perspective view of an embodiment of the present reference electrode.

As illustrated in FIGS. 1 and 2, counter electrode 30 is preferably shaped in the general form of an annulus or ring. As illustrated in FIGS. 1 and 3, reference electrode 20 is preferably shaped in a generally circular form (that is, in the general shape of a disk). Because counter electrode 30 and reference electrode 20 are preferably fabricated from the same electrically conductive carbon, counter electrode 30 and reference electrode 20 may be manufactured in a single process. In that regard, reference electrode 20 may be formed by the removal of the central, generally circular portion of electrically conductive carbon from a larger diameter, generally circular portion of electrically conductive carbon when forming annular counter electrode 30. As clear to those skilled in the art, however, counter electrode 30, reference electrode 20 and working electrode 10 of electrochemical sensor 1 can be fabricated in many different shapes.

Preferably, electrochemical nitrogen dioxide sensor 1 is subjected to a "cook-down" or "equilibration" period before use thereof to provide an adequately stable and low baseline. During the cook-down or equilibration period, electrochemical sensor 1 is stored at ambient conditions for a defined period of time. As common in the art, electrochemical sensor 1 is preferably maintained at operating potential during the cook-down period. As the operating potential of the electrochemical sensor 1 is preferably zero (0) volts, working electrode 10 and reference electrode 20 are preferably electrically shorted during the cook-down period.

Preferably, a substantially stable baseline in the range of approximately −0.7 to +0.4 $\mu$A is achieved during the cook-down period. It has been found that a cook-down period of approximately sixteen (16) hours is sufficient to provide an adequate baseline for electrochemical nitrogen dioxide sensor 1. Briefer cook-down periods have not yet been investigated, however. Electrochemical nitrogen dioxide sensors 1 used in the studies discussed below were subjected to a five-day cook-down period.

The present studies were performed under computer control in which sixteen (16) sensors could be tested simultaneously. A baseline reading for each sensor was established as the sensor output after a ten-minute exposure to air (0 ppm nitrogen dioxide). In testing for nitrogen dioxide concentration, air was first applied to electrochemical sensors 1 for ten (10) minutes followed by application of air having a known concentration of nitrogen dioxide (for example, 20 ppm nitrogen dioxide) for 10 minutes.

Response time and response time ratio (RTR) are empirical measures of the speed of response of a sensor and are critically dependent on the manner in which the test is performed (for example, the length of time the experiment lasts and/or the time at which the sensor reaches 100% of its final output). In the present studies, both response time and RTR were based upon a ten (10) minute exposure to test gas. RTR was calculated by dividing (i) the sensor output after one (1) minute of exposure to nitrogen dioxide test gas by (ii) the sensor output after ten (10) minutes of exposure to nitrogen dioxide test gas. Based upon a ten-minute test, RTR is also the percentage of final response (that is, response or output obtained after ten minutes) obtained in one minute. Response time was generally tabulated as the 90% response time ($t_{90}$) unless otherwise indicated. The $t_{90}$ response time is the time, in seconds, required for the sensor to reach 90% of the response or output obtained after ten minutes of exposure to test gas. The sensitivity (in units of $\mu$A/ppm $NO_2$) was established as the sensor output after ten (10) minutes of exposure to nitrogen dioxide.

Table 1 sets forth the results of several studies performed with a number of carbons used for working electrode 10, reference electrode 20 and counter electrode 30. Each of working electrode 10, reference electrode 20 and counter electrode 30 in a particular study were fabricated from the same carbon as indicated. In general, the supplier of the carbons is also provided in Table 1. The concentration of nitrogen dioxide in the test gas used in the studies of Table 1 was 10 ppm. The electrolyte used in the studies of Table 1 was $H_2SO_4$.

All the sensor cells in the studies set forth in Table 1 had a pattern of five (5) ⅛ inch diameter inlet holes to allow the test gas to enter the sensor cells. As clear to one of ordinary skill in the art, sensitivity can be increased by increasing the total surface area of such inlet holes to allow more gas to enter the sensor cell.

TABLE 1

| ELECTRODE MATERIAL | AVG SENS. $\mu$A/ppm | AVG. RTR OR RESPONSE TIME ($t_{90}$) | RESISTANCE RANGE (k$\Omega$) | SPECIFIC SURFACE $m^2/g$ | CARBON BASE | ACTIVATION |
|---|---|---|---|---|---|---|
| Pica USA (North American Carbon) | | | | | | |
| NAC | 0.49 | 0.29 | 6.0–17.3 | 1471 | COCONUT | STEAM |
| NAC GX203 | 0.66 | >4 min. | N/A | 940 | COCONUT | STEAM |
| West Varco | | | | | | |
| Nuchar SA 20 | No Response | 3.63 | NC | 1746 | WOOD | ACID $H_3PO_4$ |
| Nuchar BX-MP40 | 0.49 | 0.27 | 8.6–47.6 | 1331 | WOOD | ACID $H_3PO_4$ |
| Nuchar WV A1100 | No Response | 6.54 | NC | 1636 | WOOD | ACID $H_3PO_4$ |
| Calgon Carbon | | | | | | |
| Type C Pulv. | 0.60 | 0.42 | 5.1–12.5 | 946 | COAL, BITUM. | THERMAL |
| Type 114A AWD | 0.40 | 0.25 | 63–180 | 822 | COAL | THERMAL |
| Type BPL | 0.46 | 0.26 | 11.4–32.2 | 1086 | COAL, BITUM. | THERMAL |
| Type BL Pulv. | 0.56 | 0.55 | 5.1–10.6 | 1034 | COAL, BITUM. | THERMAL |
| Type RFMC | | | | 976 | COCONUT | THERMAL |

TABLE 1-continued

| ELECTRODE MATERIAL | AVG SENS. μA/ppm | AVG. RTR OR RESPONSE TIME ($t_{90}$) | RESISTANCE RANGE (kΩ) | SPECIFIC SURFACE $m^2/g$ | CARBON BASE | ACTIVATION |
|---|---|---|---|---|---|---|
| | | Johnson Matthey | | | | |
| JMAC | 0.75 | 0.86 | 2.6–8.3 | 800–900 | | |
| JMGr | 0.31 | 0.88 | N/A | | | |
| | | Miscellaneous Carbons | | | | |
| GRAPHITE | 0.25 | 0.96 | 6.7–29.8 | 4.6 | N/A | N/A |
| SGL-EG31 | 0.41 | 0.89 | .20–.70 | 13.4 | GRAPHITE | N/A |
| SGL-EG32 | 0.23 | 0.91 | .26–1.0 | | GRAPHITE | N/A |
| PUR-1 | 0.37 | 0.26 | 3.7–22.5 | 802 | | |
| | | Cabot | | | | |
| REGAL-250 | 0.31 | 0.91 | .28–.6 | 50 | OIL | N/A |
| REGAL-330 | 0.61 | 0.91 | .46–.88 | 86–94 | OIL | N/A |
| BP 800 | 0.74 | 0.80 | .48–.65 | 210–260 | OIL | N/A |
| BP 2000 | 0.85 | 0.67 | 3.6–6.3 | 1526 | OIL | N/A |
| BP 1100 | 0.59 | 0.62 | 3.4–9.0 | 240–290 | OIL | N/A |
| | | American Norrit (Aldrich) | | | | |
| DARCO 12-20 | 1.10 | — | 15–61 | 623 | COAL, LIGN | STEAM |
| DARCO KB | No Response | — | NC | 1418 | WOOD | ACID $H_3PO_4$ |
| DARCO G-60 | 1.50 | 75–80 sec | 5.2–11.7 | 850 | PROPRIETARY | STEAM |
| NORIT RO | 1.68 | 50–60 sec | 1.6–5.8 | 1100–1200 | PEAT | STEAM |
| NORIT A | 1.50 | — | 6.9–34.6 | | PEAT | STEAM |

As seen in Table 1, electrochemical sensors under the present invention are preferably fabricated from carbons having relatively low resistance and relatively high surface area. Preferably, such sensors are fabricated from carbons with resistances in the range of approximately 0.2 kΩ to 180 kΩ. More preferably, the carbons have resistances in the range of approximately 0.3 kΩ to 50 kΩ. Most preferably, the carbons have resistances in the range of approximately 0.4 kΩ to 9.0 kΩ. Such resistances were measured with an ohmmeter, using a standard two-probe technique as known in the art wherein the probes were placed approximately 1.5 cm apart upon the surface of the electrode.

Preferably, the carbons have specific surfaces in the range of approximately 4.6 $m^2/g$ to 1500 $m^2/g$. More preferably, the carbons have specific surfaces in the range of approximately 50 $m^2/g$ to 1500 $m^2/g$. Most preferably, the carbons have specific surfaces in the range of approximately 50 $m^2/g$ to 900 $m^2/g$.

As also seen in Table 1, certain activated carbons provided very good results. Of these activated carbons, the Johnson Matthey JMAC carbon and the American Norrit NORIT RO activated carbons exhibited a very good combination of high sensitivity and quick response time. However, the source/processing of the carbon is not considered crucial to the present invention provided the carbon exhibits a suitable resistance and a suitable surface area. The "best" carbon for use in a sensor for a particular application will, of course, depend upon the best combination of handling (for example, fabrication) characteristics, cost, sensitivity, and response time as defined by that application.

The electrochemical sensors of the present invention were found to provide a substantially linear signal over at least the range of approximately 0.0 to 300 ppm $NO_2$. In that regard, the test equipment used in the present studies had an upper limit of 300 ppm.

The response time of the present sensors was found to be somewhat dependent on the age of the sensor. The response times of individual sensors were found to improve (that is, decrease) over the first month of sensor life. For example, the response time for a newly fabricated sensor comprising the Johnson Matthey JMAC carbon was found to be approximately 90% at about 90 seconds (that is, $t_{90}=90$ seconds), whereas the response time was found to be approximately 90% at about 45 seconds ($t_{90}=45$ seconds) for a one-month old sensor fabricated from that carbon.

The sensitivity of the present sensors was found to be affected by humidity. Sensitivity was found to decrease if the sensor was stored in low humidity, whereas sensitivity was found to increase if the sensor was stored in a humid environment. In general, sensitivity was found to decrease if the sensors were stored in an environment having a relative humidity of less than approximately 15%. Preferably, therefore, the sensors of the present invention are stored in an environment having a relative humidity in the range of approximately 15 to 90%. It is believed that the drop in sensor sensitivity at low humidity is a result of loss of solution contact. This "drying" and the resultant sensitivity loss at low humidity are reversible upon exposure of the sensor to ambient conditions in which the relative humidity is preferably in the range of approximately 15 to 90%.

The results of several interferent studies are set forth in Table 2 using sensors fabricated from the Johnson Matthey JMAC carbon. The data provided for each interferent gas correspond to the sensor output (that is, the indicated concentration of nitrogen dioxide in ppm) upon exposure of the sensor to 100 ppm of the interferent gas. In Table 2, the results achieved with the present sensor are compared to the results achieved with Nitrogen Dioxide CiTicel sensors available from City Technology. The data provided for the City Technology sensors were taken from the corresponding City Technology technical manual. The results indicate that the present sensor is less susceptible to erroneous results arising from the presence of the interferent gases studied than the City Technology sensor. Given the relatively low electrocatalytic activity of carbon for most reactions, this result is expected regardless of the choice of carbon for the electrodes of the present invention.

TABLE 2

| | $NO_2$ | CO | NO | $H_2S$ | $SO_2$ | HCN | $CO_2$ | HCl | $NH_3$ | $H_2$ | $CH_4$ | $C_2H_4$ | $Cl_2$ | EtOH |
|---|---|---|---|---|---|---|---|---|---|---|---|---|---|---|
| Present Sensor | 100 | 0 | 0 | −4 | 0 | 0 | 0 | 0 | 0 | 0 | 0 | 0 | 68 | 0 |
| City Technology Sensor | 100 | 0 | 0 | −20 | <−.5 | <1 | — | 0 | — | 0 | — | 0 | 90 | — |

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An electrochemical gas sensor for the detection of nitrogen dioxide, comprising: a housing, the housing having disposed therein a working electrode, a reference electrode and a counter electrode, the electrochemically active surface of the working electrode consisting essentially of an electrically conductive carbon, the electrochemically active surface of the counter electrode consisting essentially of an electrically conductive carbon, electrical connection being maintained between the working electrode and the counter electrode via an electrolyte present within the housing, the electrolyte being selected such that nitrogen dioxide from an environment in fluid connection with the sensor is transported to the working electrode for direct reduction of the nitrogen dioxide, the electrochemical gas sensor further comprising circuitry whereby the potential difference between the working electrode and a carbon/air reference electrode is maintained at about 0 volt.

2. The electrochemical gas sensor of claim 1, wherein the reference electrode is fabricated from an electrically conductive carbon.

3. The electrochemical gas sensor of claim 2 wherein the counter electrode is formed in the shape of an annulus.

4. The electrochemical gas sensor of claim 3 wherein the reference electrode comprises the cut out, generally circular, central portion of the annular counter electrode.

5. The electrochemical gas sensor of claim 2 wherein each of the working electrode, the counter electrode and the reference electrode is fabricated from the same electrically conductive carbon.

6. The electrochemical gas sensor of claim 1 wherein the electrically conductive carbon from which the counter electrode is fabricated has a resistance in the range of approximately 0.2 k$\Omega$ to 180 k$\Omega$.

7. The electrochemical gas sensor of claim 6 wherein the electrically conductive carbon from which the counter electrode is fabricated has a resistance in the range of approximately 0.4 k$\Omega$ to 9 k$\Omega$.

8. The electrochemical gas sensor of claim 1 wherein the electrically conductive carbon from which the counter electrode is fabricated has a specific surface in the range of approximately 4.6 m$^2$/g to 1500 m$^2$/g.

9. The electrochemical gas sensor of claim 8 wherein the electrically conductive carbon from which the counter electrode is fabricated has a specific surface in the range of approximately 50 m$^2$/g to 900 m$^2$/g.

10. An electrochemical gas sensor for the detection of nitrogen dioxide, comprising: a housing, the housing having disposed therein a working electrode, a reference electrode and a counter electrode, the electrochemically active surface of the working electrode being fabricated from an electrically conductive carbon without a metallic electrocatalyst thereon, the electrochemically active surface of the counter electrode being fabricated from an electrically conductive carbon without a metallic electrocatalyst thereon, electrical connection being maintained between the working electrode and the counter electrode via an electrolyte present within the housing, the electrolyte being selected such that nitrogen dioxide from an environment in fluid connection with the sensor is transported to the working electrode for direct reduction of the nitrogen dioxide, the electrochemical gas sensor further comprising circuitry whereby the potential difference between the working electrode and a carbon/air reference electrode is maintained at about 0 volt.

11. The electrochemical gas sensor of claim 10, wherein the reference electrode is fabricated from an electrically conductive carbon.

12. The electrochemical gas sensor of claim 11 wherein the counter electrode is formed in the shape of an annulus.

13. The electrochemical gas sensor of claim 12 wherein the reference electrode comprises the cut out, generally circular, central portion of the annular counter electrode.

14. The electrochemical gas sensor of claim 11 wherein each of the working electrode, the counter electrode and the counter electrode is fabricated from the same electrically conductive carbon.

15. The electrochemical gas sensor of claim 10 wherein the electrically conductive carbon from which the counter electrode is fabricated has a resistance in the range of approximately 0.2 k$\Omega$ to 180 k$\Omega$.

16. The electrochemical gas sensor of claim 15 wherein the electrically conductive carbon from which the counter electrode is fabricated has a resistance in the range of approximately 0.4 k$\Omega$ to 9 k$\Omega$.

17. The electrochemical gas sensor of claim 10 wherein the electrically conductive carbon from which the counter electrode is fabricated has a specific surface in the range of approximately 4.6 m$^2$/g to 1500 m$^2$/g.

18. The electrochemical gas sensor of claim 17 wherein the electrically conductive carbon from which the counter electrode is fabricated has a specific surface in the range of approximately 50 m$^2$/g to 900 m$^2$/g.

19. An electrochemical gas sensor for the detection of nitrogen dioxide, comprising: a housing, the housing having disposed therein a working electrode, a reference electrode and a counter electrode, the electrochemically active surface of the working electrode consisting essentially of an electrically conductive carbon, the electrochemically active surface of the counter electrode consisting essentially of an electrically conductive carbon, the electrochemically active surface of the reference electrode consisting essentially of an electrically conductive carbon, electrical connection being maintained between the working electrode and the counter electrode via an electrolyte present within the housing, the working electrode and the reference electrode being electrically connected to a circuit adapted to maintain the potential difference between the working electrode and the reference electrode at about 0 volt.

* * * * *